United States Patent
Liu et al.

(10) Patent No.: US 11,358,943 B2
(45) Date of Patent: Jun. 14, 2022

(54) METHOD FOR PREPARING FURFURAL

(71) Applicant: GUANGZHOU YINNOVATOR BIOTECH CO., LTD., Guangzhou (CN)

(72) Inventors: Yunsi Liu, Guangzhou (CN); Ruizhe Zhang, Guangzhou (CN)

(73) Assignee: GUANGZHOU YINNOVATOR BIOTECH CO., LTD., Guangzhou (CN)

(*) Notice: Subject to any disclaimer, the term of this patent is extended or adjusted under 35 U.S.C. 154(b) by 90 days.

(21) Appl. No.: 17/056,927

(22) PCT Filed: Sep. 26, 2019

(86) PCT No.: PCT/CN2019/108189
§ 371 (c)(1),
(2) Date: Nov. 19, 2020

(87) PCT Pub. No.: WO2020/192053
PCT Pub. Date: Oct. 1, 2020

(65) Prior Publication Data
US 2021/0206737 A1    Jul. 8, 2021

(30) Foreign Application Priority Data

Mar. 27, 2019 (CN) .......................... 201910237443.5

(51) Int. Cl.
*C07D 307/50* (2006.01)
(52) U.S. Cl.
CPC ................................. *C07D 307/50* (2013.01)
(58) Field of Classification Search
CPC .................................................. C07D 307/50
See application file for complete search history.

(56) References Cited

FOREIGN PATENT DOCUMENTS

| CN | 102659723 A | 9/2012 |
| CN | 103193737 A | 7/2013 |
| CN | 106536495 A | 3/2017 |
| CN | 106536496 A | 3/2017 |
| CN | 109748895 A | 5/2019 |

OTHER PUBLICATIONS

Chinese-language International Search Report and Written Opinion issued in counterpart PCT Application No. PCT/CN2019/108189 dated Dec. 30, 2019, with English translation (nine (9) pages).

*Primary Examiner* — Golam M Shameem
(74) *Attorney, Agent, or Firm* — David S. Bradin; Nexsen Pruet, PLLC

(57) ABSTRACT

Provided is a method for preparing furfural. The method comprises: mixing a plant raw material and an acid containing a —$SO_3H$ functional group for pre-treating, then mixing same with an organic acid, cooking same, and then subjecting same to solid-liquid separation, so as to obtain a hemicellulose sugar solution; introducing the resulting hemicellulose sugar solution from the upper part of a reaction kettle, and at the same time, introducing an acetic acid steam from the lower part of the reaction kettle, such that the sugar solution and the acetic acid steam come into contact in a counter-current manner and react so as to form a furfural steam; after the reaction is completed, discharging the furfural steam from the upper part of the reaction kettle; and cooling same so as to obtain a solution containing furfural. In the method, by means of firstly pre-treating the plant raw material using the acid containing a —$SO_3H$ functional group, and then cooking same with the organic acid, the hydrolysis rate of pentosan in a hemicellulose can reach 99% or more, thus achieving efficient use of valuable substances in the raw material. In addition, the method relates to a process for discharging the furfural steam in batches and semi-continuously, has an improved furfural production rate, which rate can reach 65-75%, and has good economic benefits and application prospects.

15 Claims, No Drawings

METHOD FOR PREPARING FURFURAL

CROSS REFERENCE TO RELATED APPLICATIONS

This application is a 35 U.S.C. § 371 U.S. national phase entry of International Application No. PCT/CN2019/108189 having an international filing date of Sep. 26, 2019, which claims the benefit of Chinese Application No. 201910237443.5 filed Mar. 27, 2019, the contents of each of which are incorporated herein by reference in their entireties.

TECHNICAL FIELD

The present application relates to the field of furfural preparation and for example, to a method for preparing furfural.

BACKGROUND

The production of furfural typically employs pentosane from plant raw materials, as plant fibers primarily contain cellulose, hemicellulose and lignin. Pentosane contained in the hemicellulose is first hydrolyzed to generate pentose, and then the pentose is dehydrated to generate furfural.

At present, in the industrial production of furfural, a strong acid is generally used as the catalyst. In the process of hydrolysis, the furfural and by-product volatile substances produced by hydrolysis are entrained from a hydrolysis pot by high pressure water vapor to form an aldehyde gas. The aldehyde gas generally contains 4-6% furfural, 1-2% acetic acid, and a small amount of low-boiling-point substances. After condensing, the aldehyde gas enters a primary distillation column, and an azeotrope of furfural and water is yielded at the bottom while an industrial wastewater containing acetic acid and a small amount of furfural is discharged from the head of the primary distillation column.

CN102329287A discloses a new process for preparing furfural using a xylose mother solution and a special equipment thereof. In the preparation process, the xylose mother solution and sulfuric acid solution are first weighed in parts by weight to obtain a mixture, the mixture is added to a reaction kettle to which the furfural conversion-distillation column belongs, the vapor is introduced into the reaction kettle through a direct steam heating distributor, the xylose is dehydrated into furfural under the action of sulfuric acid; after the reaction is accomplished, the steam is stopped flowing to the reaction kettle, the steam is transported into a jacket to heat the reaction kettle, and operations of distillation and separation are subsequently performed.

CN103193737A discloses a method for preparing furfural and co-producing lignin and cellulosic ethanol with plant materials as raw materials. The method sequentially includes the following steps: hydrolyzing hemicelluloses to prepare pentose, pre-heating a pentose solution, and carrying out steps of ejection and temperature raising, dehydration and cyclization, aldehyde vapor flash evaporation and pressure relief, distillation, and rectification separation to obtain furfural as a main distillate fraction. The method hydrolyzes the pentosan contained in the hemicellulose of plant materials to pentose by utilizing the acid fluid such as sulfuric acid, an acetic acid solution, a nitric acid solution, hydrochloric acid, and an aqueous solution of solid super acids.

CN105503790A discloses a method for preparing furfural from corncobs and corn straw serving as raw materials. The method includes: pretreating corncobs and corn straw, separating and extracting hemicellulose in the corn straw and the corncobs by using a diluted sulfuric acid solution, and finally, converting the hemicellulose into furfural at high temperature under high pressure.

CN102659723A discloses a process for preparing furfural by using agricultural by-products of high and crude fiber plants. The method includes the steps of: hydrolyzing pretreated raw materials in a hydrolyzing tank, using an acid catalyst formed by mixing sulfuric acid and phosphoric acid during the hydrolytic process; introducing high-temperature steam into the hydrolyzing tank, heating up the hydrolyzing tank, and conducting gap stripping for a hydrolysis product which is furfural; and feeding the gas-stripped furfural into a furfural phase splitter to obtain a crude furfural and a furfural residue. The process achieves raw material hydrolysis by using the acid catalyst combining sulfuric acid and phosphoric acid, which is assisted by ultrasonic treatment simultaneously, so that the productivity of the furfural is improved.

In the above processes of preparing furfural, inorganic strong acid is used as the catalyst. However, since this type of catalyst has strong acidity, waste liquids resulting from these processes can hardly be effectively dealt with, which puts great pressure on the environment. However, when the furfural is prepared with the organic acid used as the catalyst, the pentosan conversion rate is not high, which results in the waste of valuable substances in raw materials and the increases of the production cost. Furthermore, the reaction equilibrium in the preparation of furfural from hemicellulose solution is limited, and since in the conventional process of furfural preparation front the hemicellulose solution, the release time of furfural vapor is always after the time when the reaction ends, the yield of furfural is low, and the utilization rate of raw materials is not high since there is still a large part of the raw materials unreacted. Therefore, there is a need to improve the relevant processes of preparing furfural from plant materials.

SUMMARY

The following is a summary of the subject matter described herein in detail. This summary is not intended to limit the scope of the claims.

The object of the present application is to provide a method for preparing furfural, to greatly improve the hydrolysis rate of pentosan in hemicellulose while increasing the yield of furfural.

To achieve the object, the present application adopts technical solutions described below.

The present application provides a method for preparing furfural. The method includes the following steps:

(1) mixing a plant raw material with an acid containing a —SO$_3$H functional group for pretreatment;

(2) mixing a material obtained after the pretreatment in step (1) with an organic acid for digestion, and then performing solid-liquid separation to obtain a hemicellulose solution; and (3) introducing the hemicellulose solution obtained in step (2) from a upper part of a reaction kettle, while introducing acetic acid vapor from a lower part of the reaction kettle, so as to place the solution in countercurrent contact with the acetic acid vapor for a reaction to generate a furfural vapor, and after the reaction is finished, discharging the furfural vapor from the upper part of the reaction kettle and cooling to obtain a solution containing furfural.

In the present application, prior to the pretreatment in step (1), the plant raw material are pulverized, and then the pulverized material is mixed with the acid containing a —SO$_3$H functional group for pretreatment.

According to the present application, the acid containing the —SO$_3$H functional group in step (1) is methanesulfonic acid and/or ethanesulfonic acid.

According to the present application, the pretreatment in step (1) is performed at room temperature.

According to the present application, a period for the pretreatment in step (1) is 0.5 to 1 hours (h), for example, 0.5 h, 0.6 h, 0.7 h, 0.8 h, 0.9 h, 1 h, or any specific numerical value between the above numerical values, which for the sake of length and simplicity, will not be exhaustively listed in the present application.

According to the present application, the organic acid in step (2) is at least one of formic acid, acetic acid, or butanoic acid, for example, any one of formic acid, acetic acid, or butanoic acid, and a typical but non-limiting combination is a combination of formic acid and acetic acid, a combination of formic acid and butanoic acid, a combination of acetic acid and butanoic acid, or a combination of formic acid, acetic acid and butanoic acid.

According to the present application, a temperature for the digestion in step (2) is 90° C. to 150° C., for example, 90° C., 95° C., 100° C., 105° C., 110° C., 115° C., 120° C., 125° C., 130° C., 135° C., 140° C., 145° C., 150° C., or any specific numerical value between the above numerical values, which for the sake of length and simplicity, will not be exhaustively listed in the present application.

According to the present application, a period for the digestion in step (2) is 0.1 to 1.5 h, for example, 0.1 h, 0.3 h, 0.5 h, 0.8 h, 1 h, 1.3 h, 1.5 h, or any specific numerical value between the above numerical values, which for the sake of length and simplicity, will not be exhaustively listed in the present application.

According to the present application, a solid-to-liquid mass ratio of the material obtained after the pretreatment to the organic acid in step (2) is 1:(5-25), for example, 1:5, 1:8, 1:10, 1:13, 1:15, 1:18, 1:20, 1:23, 1:25, or any specific numerical value between the above numerical values, which for the sake of length and simplicity, will not be exhaustively listed in the present application.

According to the present application, a mass concentration of the organic acid in step (2) is 50% to 95%, for example, 50%, 55%, 60%, 65%, 70%, 75%, 80%, 85%, 90%, 95%, or any specific numerical value between the above numerical values, which for the sake of length and simplicity, will not be exhaustively listed in the present application.

According to the present application, the reaction kettle in step (3) is a reaction kettle having multiple layers of trays.

According to the present application, the hemicellulose has a temperature of 160° C. to 200° C. when entering the reaction kettle in step (3), for example, 160° C., 165° C., 170° C., 175° C., 180° C., 185° C., 190° C., 195° C., 200° C., or any specific numerical value between the above numerical values, which for the sake of length and simplicity, will not be exhaustively listed in the present application.

According to the present application, a temperature of the acetic acid vapor in step (3) is 230° C. to 280° C., for example, 230° C., 235° C., 240° C., 245° C., 250° C., 255° C., 260° C., 265° C., 270° C., 275° C., 280° C., or any specific numerical value between the above numerical values, which for the sake of length and simplicity, will not be exhaustively listed in the present application.

According to the present application, a mass concentration of acetic acid in the acetic acid vapor in step (3) is 10% to 20%, for example, 10%, 11%, 12%, 13%, 14%, 15%, 16%, 17%, 18%, 19%, 20%, or any specific numerical value between the above numerical values, which for the sake of length and simplicity, will not be exhaustively listed in the present application.

According to the present application, in step (3), once the production of furfural reaches 40% to 60% of that in the case of complete reaction, the furfural vapor is discharged, and the reaction continues with the supplement of the hemicellulose solution and the acetic acid vapor.

In the conventional process of furfural preparation, the furfural vapor is released all at once, and the release time of furfural vapor is always after the time when the reaction ends, so the yield of furfural is 35% to 45%, which is low. In the present application, a process of releasing the furfural vapor for multiple times, that is, the furfural vapor starts to release before the reaction endpoint (the reaction is carried out from 40% to 60%), and this semi-continuous release manner can make the reaction more thorough, such that the yield of furfural can be increased accordingly.

According to the present application, after the solution containing furfural obtained in step (3) is rectified, the resulting distillate contains acetic acid, and the acetic acid is heated to form an acetic acid vapor for use in a furfural preparation process.

As an optional technical solution, the method for preparing furfural provided in the present application includes the following steps:

(1) mixing a plant raw material with an acid containing a —SO$_3$H functional group for pretreatment for 0.5 to 1 hours, the acid containing the —SO$_3$H functional group being methanesulfonic acid and/or ethanesulfonic acid;

(2) mixing a material obtained after the pretreatment in step (1) with an organic acid with a mass concentration of 50% to 95% in a solid-to-liquid mass ratio of 1:(5-25) for digestion at 90° C. to 150° C. for 0.1 to 0.5 hours, and then performing solid-liquid separation to obtain a hemicellulose solution, the organic acid being at least one of formic acid, acetic acid or butanoic acid; and (3) heating the hemicellulose solution obtained in step (2) up to 160° C. to 200° C. before introducing to the reaction kettle from a upper part of a reaction kettle having multiple layers of trays, while introducing acetic acid vapor having a mass concentration of 10% to 20% and a temperature of 230° C. to 280° C. from a lower part of the reaction kettle, so as to place the solution in countercurrent contact with the acetic acid vapor for a reaction to generate a furfural vapor, once production of furfural reaches 40% to 60% of that in case of complete reaction, discharging the furfural vapor while supplementing the hemicellulose solution and the acetic acid vapor to make the reaction continue, cooling the discharged furfural vapor to obtain a solution containing furfural, rectifying the solution containing furfural to obtain distillate containing acetic acid, and heating the acetic acid to form the acetic acid vapor for use in the furfural preparation process.

Compared with the related art, the present application has at least following beneficial effects.

(1) In the present application, the plant raw material is first pre-treated by utilizing the acid containing —SO$_3$H functional group at room temperature, and then the pre-treated plant raw material is digested by utilizing organic acid such that pentosane in the hemicellulose is hydrolyzed to generate pentose, and hence a hydrolysis rate of pentosan in the hemicellulose can be 99% or higher, thereby realizing efficient utilization of valuable materials in the raw material and reducing production costs.

(2) In the present application, the process of semi-continuous release of furfural vapor in batches is adopted to make the preparation reaction more thorough, and the yield of furfural is 65% to 75%, which is about 30% higher than that of the process of releasing all furfural vapor at once in the related art; and this method also favors continuous and stable production and improves the efficiency of production process.

(3) In the present application, the distillate is heated to form the acetic acid vapor which is further used in the furfural preparation process, thereby the cost for processing the distillate is saved while the utilization rate of raw material is improved.

Other aspects can be understood after the detailed description is read and understood.

DETAILED DESCRIPTION

For a better understanding of the present application, examples of the present application are listed below. Those skilled in the art should understand that the examples described herein are merely used for a better understanding of the present application and should not be construed as specific limitations to the present application.

The plant raw materials used in the specific embodiments of the present application are selected from straw, corncobs, bark, bamboos, corncobs, cottonseed hulls, cane bagasse, bran and the like, but are not limited thereto, and the plant raw materials of other organisms are also applicable to the present application.

In the present application, prior to the pretreatment, the above plant raw material is pulverized into small pieces of about 2*1.5*0.5 cm, and then the pretreatment operation is performed.

In the specific embodiments of the present application, the addition amount of the acid containing —$SO_3H$ functional group is not specifically limited as long as the plant raw materials are immersed by the acid in the pretreatment process, and after the pretreatment is completed, solid-liquid separation is performed, with the pre-treated raw material used in the subsequent furfural preparation operation, such that the acid containing a —$SO_3H$ functional group can be reused.

Typical but non-limiting specific examples of the present application are described below.

EXAMPLE 1

(1) Corncobs were immersed in methanesulfonic acid and then pre-treated for 0.5 h at room temperature, materials obtained after the pre-treating were mixed with formic acid with a mass concentration of 50% in a solid-to-liquid mass ratio of 1:25 for digestion for 0.5 h at an increased temperature of 150° C. to obtain a slurry, and the resulting slurry was filtered to obtain a hemicellulose solution.

(2) The hemicellulose solution obtained in step (1) was heated to 180° C. before being introduced to the reaction kettle from the upper part of the reaction kettle having multiple layers of trays, while acetic acid vapor having a mass concentration of 20% and a temperature of 250° C. was introduced from the lower part of the reaction kettle, so as to place the solution in countercurrent contact with the acetic acid vapor for a reaction to generate furfural vapor, once production of the furfural reached 50% of that in case of complete reaction, the furfural vapor was discharged while the hemicellulose solution and the acetic acid vapor were supplemented to make the reaction continue, the discharged furfural vapor was cooled to obtain a solution containing furfural, the solution containing furfural was rectified to obtain distillate containing acetic acid, and the acetic acid was heated to form the acetic acid vapor for use in the furfural preparation process.

The hydrolysis rate of pentosan in the plant raw materials was determined to be 99.3%, with a 72% yield of furfural.

EXAMPLE 2

(1) Cane bagasse was immersed in ethanesulfonic acid and then pre-treated for 1 h at room temperature, materials obtained after the pre-treating were mixed with acetic acid with a mass concentration of 95% in a solid-to-liquid mass ratio of 1:5 for digestion for 1.5 h at an increased temperature of 90° C. to obtain a slurry, and the resulting slurry was filtered to obtain a hemicellulose solution.

(2) The hemicellulose solution obtained in step (1) was heated to 200° C. before being introduced to the reaction kettle from the upper part of the reaction kettle having multiple layers of trays, while acetic acid vapor having a mass concentration of 15% and a temperature of 280° C. was introduced from the lower part of the reaction kettle, so as to place the solution in countercurrent contact with the acetic acid vapor for a reaction to generate furfural vapor, once production of the furfural reached 40% of that in case of complete reaction, the furfural vapor was discharged while the hemicellulose solution and the acetic acid vapor were supplemented to make the reaction continue, the discharged furfural vapor was cooled to obtain a solution containing furfural, the solution containing furfural was rectified to obtain distillate containing acetic acid, and the acetic acid was heated to form the acetic acid vapor for use in the furfural preparation process.

The hydrolysis rate of pentosan in the plant raw materials was determined to be 99.5%, with a 66% yield of furfural.

EXAMPLE 3

(1) Bamboos were immersed in ethanesulfonic acid and then pre-treated for 0.8 h at room temperature, materials obtained after the pre-treating were mixed with butanoic acid with a mass concentration of 70% in a solid-to-liquid mass ratio of 1:15 for digestion for 1 h at an increased temperature of 100° C. to obtain a slurry, and the resulting slurry was filtered to obtain a hemicellulose solution.

(2) The hemicellulose solution obtained in step (1) was heated to 180° C. before being introduced to the reaction kettle from the upper part of the reaction kettle having multiple layers of trays, while acetic acid vapor having a mass concentration of 10% and a temperature of 230° C. was introduced from the lower part of the reaction kettle, so as to place the solution in countercurrent contact with the acetic acid vapor for a reaction to generate furfural vapor, once production of the furfural reached 55% of that in case of complete reaction, the furfural vapor was discharged while the hemicellulose solution and the acetic acid vapor were supplemented to make the reaction continue, the discharged furfural vapor was cooled to obtain a solution containing furfural, the solution containing furfural was rectified to obtain distillate containing acetic acid, and the acetic acid was heated to form the acetic acid vapor for use in the furfural preparation process.

The hydrolysis rate of pentosan in the plant raw materials was determined to be 99.5%, with a 75% yield of furfural.

EXAMPLE 4

(1) Corn straw was immersed in a mixed liquor of methanesulfonic acid and ethanesulfonic acid and then pretreated for 0.7 h at room temperature, materials obtained after the pre-treating were mixed with acetic acid with a mass concentration of 60% in a solid-to-liquid mass ratio of 1:20 for digestion for 1 h at an increased temperature of 95° C. to obtain a slurry, and the resulting slurry was filtered to obtain a hemicellulose solution.

(2) The hemicellulose solution obtained in step (1) was heated to 170° C. before being introduced to the reaction kettle from the upper part of the reaction kettle having multiple layers of trays, while acetic acid vapor having a mass concentration of 13% and a temperature of 270° C. was introduced from the lower part of the reaction kettle, so as to place the solution in countercurrent contact with the acetic acid vapor for a reaction to generate furfural vapor, once production of the furfural reached 60% of that in case of complete reaction, the furfural vapor was discharged while the hemicellulose solution and the acetic acid vapor were supplemented to make the reaction continue, the discharged furfural vapor was cooled to obtain a solution containing furfural, the solution containing furfural was rectified to obtain distillate containing acetic acid, and the acetic acid was heated to form the acetic acid vapor for use in the furfural preparation process.

the hydrolysis rate of pentosan in the plant raw materials was determined to be 99.6%, with a 70% yield of furfural.

EXAMPLE 5

(1) Bark was immersed in methanesulfonic acid and then pre-treated for 0.6 h at room temperature, materials obtained after the pre-treating were mixed with acetic acid with a mass concentration of 75% in a solid-to-liquid mass ratio of 1:12 for digestion for 1 h at an increased temperature of 110° C. to obtain a slurry, and the resulting slurry was filtered to obtain a hemicellulose solution.

(2) The hemicellulose solution obtained in step (1) was heated to 180° C. before being introduced to the reaction kettle from the upper part of the reaction kettle having multiple layers of trays, while acetic acid vapor having a mass concentration of 17% and at a temperature of 250° C. was introduced from the lower part of the reaction kettle, so as to place the solution in countercurrent contact with the acetic acid vapor for a reaction to generate furfural vapor, once production of the furfural reached 45% of that in case of complete reaction, the furfural vapor was discharged while the hemicellulose solution and the acetic acid vapor were supplemented to make the reaction continue, the discharged furfural vapor was cooled to obtain a solution containing furfural, the solution containing furfural was rectified to obtain distillate containing acetic acid, and the acetic acid was heated to form the acetic acid vapor for use in the furfural preparation process.

The hydrolysis rate of pentosan in the plant raw materials was determined to be 99.2%, with a 68% yield of furfural.

Comparative Example 1

The conditions were the same as those in Example 1 except that the step of pre-treating was not performed. That is, the plant raw material was directly digested by utilizing the organic acid.

The hydrolysis rate of pentosan in the plant raw materials was determined to be 85.8% in this comparative example.

Comparative Example 2

The conditions were the same as those in Example 1 except that the furfural vapor was discharged after the complete reaction of furfural in step (2).

The yield of furfural was determined to be 43% in this comparative example.

Comparative Example 3

The conditions were the same as those in Example 1 except that the methanesulfonic acid was replaced with hydrochloric acid in the pre-treating in step (1).

The hydrolysis rate of pentosan in the plant raw material was determined to be 87.3% in this comparative example.

Comparative Example 4

The conditions were the same as those in Example 1 except that the methanesulfonic acid was replaced with acetic acid in the pre-treating in step (1).

The hydrolysis rate of pentosan in the plant raw material was determined to be 86.8% in this comparative example.

It can be learned from Examples 1-5 that the method provided in the present application realized efficient utilization of valuable materials in the raw materials in the preparation process of furfural while greatly improving the yield of furfural, among which the hydrolysis rate of pentosan in plant raw materials can reach 99% or higher and the yield of furfural can reach 65% or higher.

It can be learned from Comparative example 1 that in case where the pre-treating is not performed, the hydrolysis rate of pentosan in plant raw materials is only 85.8%, significantly lower than that in Example 1, which indicates that in case where the organic acid is used as a catalyst in furfural preparation, the step of pre-treating the plant raw materials with the acid containing a —$SO_3H$ functional group can effectively promote the hydrolysis of pentosan in hemicellulose and improve the utilization rate of the raw materials.

It can be learned from Comparative example 2 that the yield of furfural was only 43% when the furfural vapor was released all at once while the yield of furfural in Example 1 was up to 72%, which was increased by 29%, which indicates that semi-continuously releasing the furfural vapor in batches can greatly increase the yield of furfural.

It can be learned from Comparative examples 3 and 4 that in case where the methanesulfonic acid was replaced with hydrochloric acid and acetic acid for pre-treating, the hydrolysis rate of pentosane in plant raw materials was only 87.3% and 86.8% respectively, which indicates that in the process of pre-treating, the acid containing a —$SO_3H$ functional group plays an irreplaceable role in improving the hydrolysis rate of pentosan.

The applicant has stated that although the detailed process equipment and flows of the present application are described through the examples described above, the present application is not limited to the detailed process equipment and flows described above, which means that the implementation of the present application does not necessarily depend on the detailed process equipment and flows described above.

What is claimed is:

1. A method for preparing furfural, comprising:
   (a) mixing a plant raw material with an acid containing a —$SO_3H$ functional group for pretreatment;
   (b) mixing a material obtained after the pretreatment in step (a) with an organic acid for digestion, and then performing solid-liquid separation to obtain a hemicellulose solution; and
   (c) introducing the hemicellulose solution obtained in step (b) from a upper part of a reaction kettle, while introducing acetic acid vapor from a lower part of the reaction kettle, so as to place the solution in countercurrent contact with the acetic acid vapor for a reaction to generate a furfural vapor, and after the reaction is finished, discharging the furfural vapor from the upper part of the reaction kettle and cooling to obtain a solution containing furfural.

2. The method according to claim 1, wherein in step (3), once production of furfural reaches 40% to 60% of that in case of complete reaction, the furfural vapor is exported, and the reaction continues with the supplement of the hemicellulose solution and the acetic acid vapor.

3. The method according to claim 1, wherein the acid containing the —SO$_3$H functional group in step (1) is methanesulfonic acid and/or ethanesulfonic acid.

4. The method according to claim 1, wherein a period for the pretreatment in step (a) is 0.5 to 1 hours.

5. The method according to claim 1, wherein the organic acid in step (b) is at least one of formic acid, acetic acid, or butanoic acid.

6. The method according to claim 1, wherein a temperature for the digestion in step (b) is 90° C. to 150° C.

7. The method according to claim 1, wherein a period for the digestion in step (b) is 0.1 to 1.5 hours.

8. The method according to claim 1, wherein a solid-to-liquid mass ratio of the material obtained after the pretreatment to the organic acid in step (b) is 1:(5-25).

9. The method according to claim 1, wherein a mass concentration of the organic acid in step (b) is 50% to 95%.

10. The method according to claim 1, wherein the reaction kettle in step (c) is a reaction kettle having a plurality of layers of trays.

11. The method according to claim 1, wherein the hemicellulose solution has a temperature of 160° C. to 200° C. when entering the reaction kettle in step (c).

12. The method according to claim 1, wherein, a temperature of the acetic acid vapor in step (c) is 230° C. to 280° C.

13. The method according to claim 1, wherein, a mass concentration of acetic acid in the acetic acid vapor in step (c) is 10% to 20%.

14. The method according to claim 1, wherein after the solution containing furfural obtained in step (c) is rectified, the resulting distillate contains acetic acid, and the acetic acid is heated to form an acetic acid vapor for use in a furfural preparation process.

15. The method according to claim 1, comprising:

(a) mixing a plant raw material with an acid containing a —SO$_3$H functional group for pretreatment for 0.5 to 1 hours, the acid containing the —SO$_3$H functional group being methanesulfonic acid and/or ethanesulfonic acid;

(b) mixing a material obtained after the pretreatment in step (a) with an organic acid with a mass concentration of 50% to 95% in a solid-to-liquid mass ratio of 1:(5-25) for digestion at 90° C. to 150° C. for 0.1 to 0.5 hours, and then performing solid-liquid separation to obtain a hemicellulose solution, the organic acid being at least one of formic acid, acetic acid or butanoic acid; and (c) heating the hemicellulose solution obtained in step (b) up to 160° C. to 200° C. before introducing to the reaction kettle from a upper part of a reaction kettle having a plurality of layers of trays, while introducing acetic acid vapor having a mass concentration of 10% to 20% and a temperature of 230° C. to 280° C. from a lower part of the reaction kettle, so as to place the solution in countercurrent contact with the acetic acid vapor for a reaction to generate a furfural vapor, once production of furfural reaches 40% to 60% of that in case of complete reaction, discharging the furfural vapor while supplementing the hemicellulose solution and the acetic acid vapor to make the reaction continue, cooling the discharged furfural vapor to obtain a solution containing furfural, rectifying the solution containing furfural to obtain distillate containing acetic acid, and heating the acetic acid to form the acetic acid vapor for use in the furfural preparation process.

\* \* \* \* \*